United States Patent [19]

Wesseling et al.

[11] 4,406,289
[45] Sep. 27, 1983

[54] DEVICE FOR THE INDIRECT, NON-INVASIVE AND CONTINUOUS MEASUREMENT OF BLOOD PRESSURE

[75] Inventors: Karel H. Wesseling, Bunnik; Wilhelmus H. Klawer, Nieuwegein, both of Netherlands

[73] Assignee: Nederlandse Centrale Organisatie voor Toegepast-Natuurwetenschappelijk, The Hague, Netherlands

[21] Appl. No.: 300,745

[22] Filed: Sep. 10, 1981

[30] Foreign Application Priority Data

Sep. 12, 1980 [NL] Netherlands .......................... 8005145

[51] Int. Cl.$^3$ .............................................. A61B 5/02
[52] U.S. Cl. .................................... 128/670; 128/672; 128/679; 128/689; 128/690
[58] Field of Search .............. 128/670, 672, 679, 680, 128/681, 682, 683, 689, 690; 137/82, 625.27

[56] References Cited

U.S. PATENT DOCUMENTS 3,063,422 11/1962 Gregowski et al. ................... 137/82
3,776,510 12/1973 Beck ............................... 137/625.27
4,172,450 10/1979 Rogers et al. ....................... 128/679

OTHER PUBLICATIONS

Yamakoshi et al., "Indirect Measurement of Instantaneous Arterial Blood Pressure in the Human Finger by the Vascular Unloading Technique", Mar. 1980.

Primary Examiner—Richard J. Apley
Assistant Examiner—George Yanulis
Attorney, Agent, or Firm—Cushman, Darby and Cushman

[57] ABSTRACT

A device for the indirect, non-invasive and continuous measurement of blood pressure in a finger by using a photo-electric plethysmograph having a pressure cuff to be placed around the finger and to be filled with fluid, an associated light source and light detector, an electronic circuit, and an electric control valve having at least one fluid flapper-nozzle system, the cuff pressure being controlled by the plethysmographic signal in closed-loop operation such that the arterial volume is maintained on a pre-adjusted value and each deviation thereof due to changes in intra-arterial pressure is compensated immediately, whereby the control valve consists of a double fluid flapper-nozzle system in balance connection, whereby a single flapper member is positioned between the oppositely arranged nozzle openings of two nozzle members and alternately opens and closes these nozzle openings, one flapper-nozzle system being used in opposite sense, and one single chamber surrounding both nozzle openings being connected to the pressure cuff.

10 Claims, 6 Drawing Figures

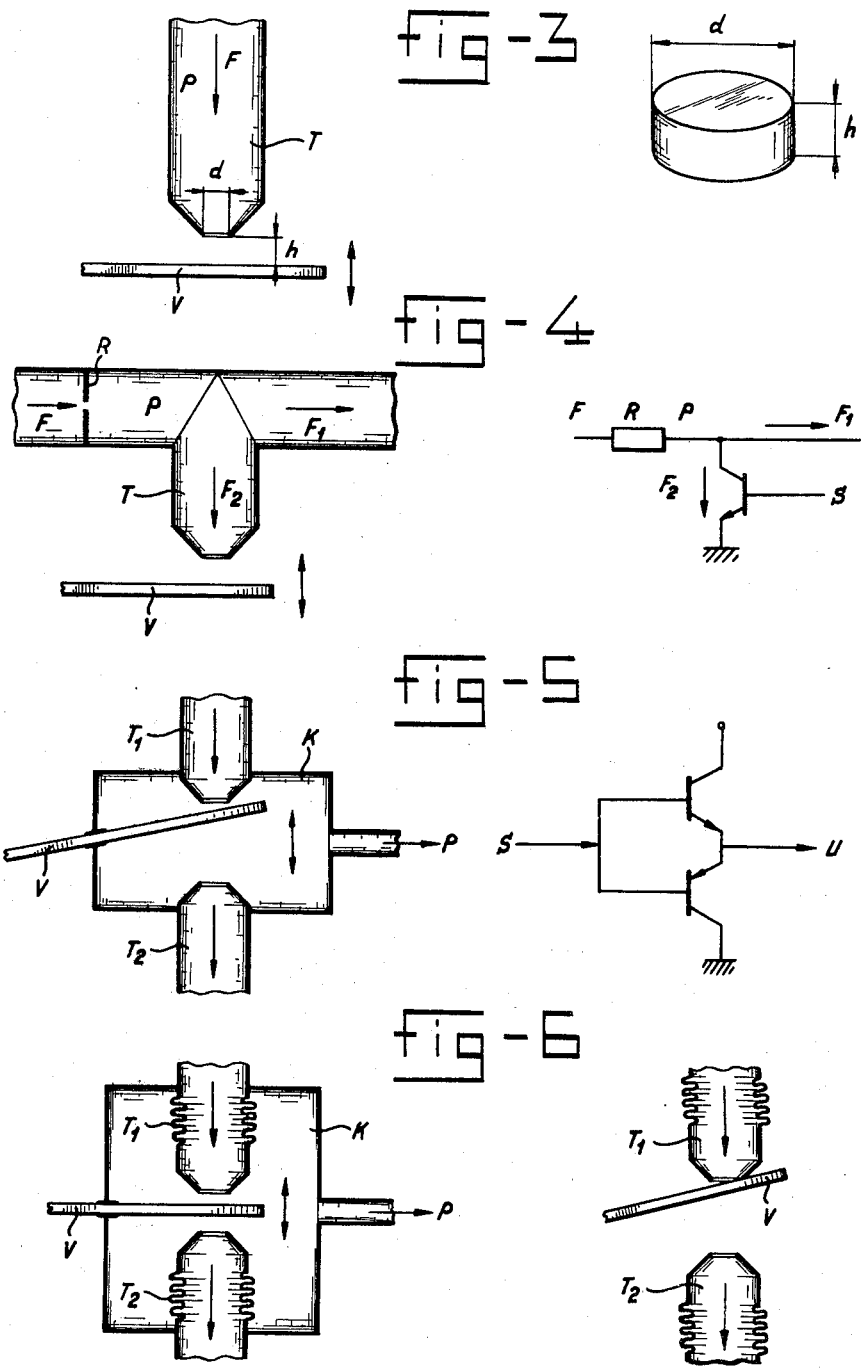

DEVICE FOR THE INDIRECT, NON-INVASIVE AND CONTINUOUS MEASUREMENT OF BLOOD PRESSURE

The invention relates to a device for the indirect, non-invasive and continuous measurement of blood pressure in a finger by using a photo-electric plethysmograph having a pressure cuff, to be placed around the finger and to be filled with fluid, and associated light source and light detector, an electronic circuit, and an electric control valve having at least one fluid flapper-nozzle system, the cuff pressure being controlled by the plethysmographic signal in closed-loop operation such that the arterial volume is maintained on a pre-adjusted value, and each deviation thereof due to changes in intra-arterial pressure is immediately compensated. Such a device is known from the article "Beitrag zur fortlaufenden indirecten Blutdruckmessung" by J. Peñáz, A. Voigt and W. Teichmann in "Zeitschrift für die gesamte innere Medizin und Ihre Grensgebiete" VEB Georg Thieme, Leipzig, Vol. 31 (1976) part 24, page 1030–1033.

Such devices are presently of great importance in the hemodynamics of hypertension, the evaluation of anti-hypertensiva, the psychophysiology of hypertension, blood pressure measurement by the patient at home, 24-hour blood pressure registration, biofeedback studies, etc. for which it is required to continuously measure arterial blood pressure in an automatic and non-invasive way.

A disadvantage in the device described in above mentioned periodical is that in case fast changes of the cuff pressure are required the control valve should be of large power owing to which a lot of air is used. It is the object of the invention to obviate said problem.

This is attained with a device of the type mentioned in the preamble such that the control valve consists of a double fluid flapper-nozzle system in balance connection, with a single flapper member positioned between oppositely arranged nozzle openings of two nozzle members, the flapper and nozzle openings being positioned such that as the flapper moves to close either nozzle it opens the other. A single chamber, enclosing both nozzle openings, is connected to the pressure cuff.

The device according to the invention is implemented to advantage such that in the control valve the walls of the nozzle members consist of resilient material by which the fluid leakage is limited while maintaining a large controlling power.

The control of the movement of the flapper member is often realized with the aid of an electro-magnetic coupling motor. However, the flapper member advantageously may also be coupled to a piezo-electric element which changes in form in response to the electric signal from the electronic circuit. Furthermore, the electric control valve may be arranged near or on the pressure cuff in order to minimize the length of the fluid connection between the said chamber and the pressure cuff.

The fluid can as well be a liquid as a gas, whereby in case of a gas preferably air is used.

The invention will be clarified in detail with reference to the drawings, in which:

FIGS. 3 and 4 are a section of a known flapper-nozzle system, an equivalent resistance-transistor diagram being indicated in FIG. 3;

FIG. 5 is a section of a double flapper-nozzle system according to the invention and a diagram of an equivalent transistor circuit; and FIG. 6 is a section of a further embodiment of the double flapper-nozzle system of FIG. 5.

Figure 1:
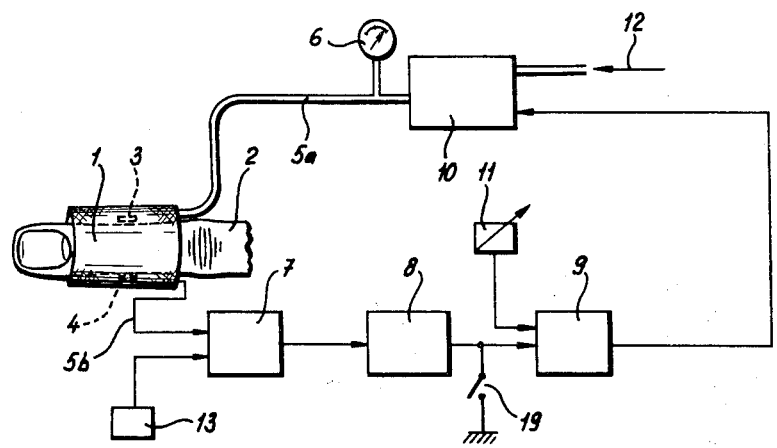
FIG. 1 is a diagram of the components used in a known device, as described by J. Penaz, for the measurement of finger blood pressure.

The general principle of the measurement is schematically indicated in FIG. 1. The photo-electric plethysmograph indicated in this figure is provided with an inflatable pressure cuff 1 which can be winded around the finger 2 and which at its inner side is provided with a light source 3 and a light detector 4. The signal being provided by the light detector 4 is supplied to a differential amplifier 7 to which other input an adjusting or compensation signal of the adjusting means 13 is supplied. The output signal of the differential amplifier 7 is supplied to a PID-circuit 8, the output signal of which is supplied to a power amplifier 9. In open-loop operation, i.e. the switch 19 being closed, the pressure adjusting signal of the adjusting means 11 is used to adjust the said power amplifier 9. The output signal of said amplifier 9 controls the electro-pneumatic transducer 10 such that the gas or air of the compressor or pressurized air container 12 is adjusted to the desired pressure, which via the line 5a is transferred to the pressure cuff. The pressure can be read off or recorded with the aid of means 6, for example by means of a pressure transducer mounted at the outlet of the electro-pneumatic transducer.

The differential amplifier 7 may consist of a field effect transistor amplifier having a separate input to compensate the mean current level of the photo-electric detector. The PID-circuit 8 may consist of an integrating amplifier, one or a plurality of differentiating amplifiers and a separate circuit to linearize the static characteristic of the valve 10. The integrating amplifier in the said control loop is required in the system to correctly track changes in the mean blood pressure level. The differentiating amplifier stages are required to stabilize the control loop at high gain.

Figure 2:
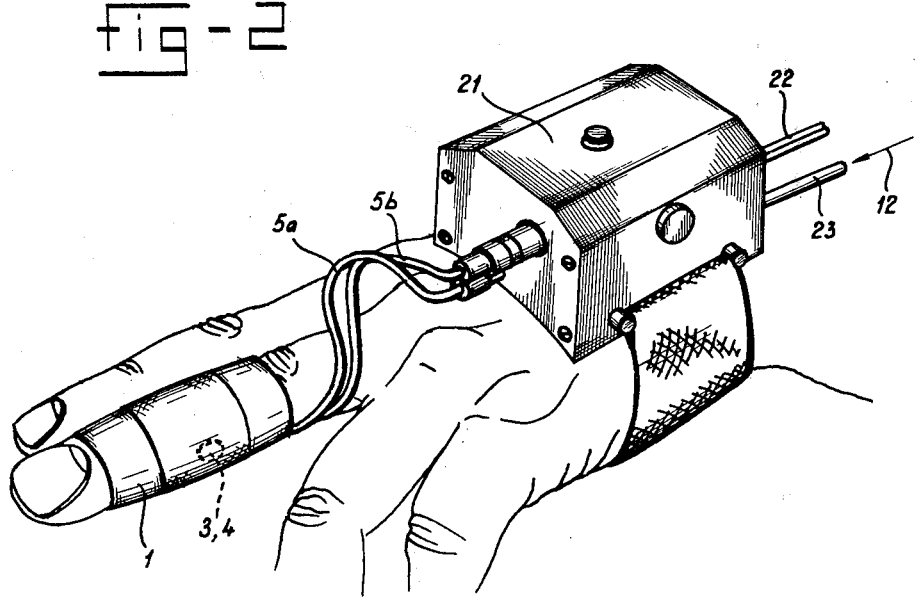
FIG. 2 is a schematic view of the photo-electric plethysmograph, arranged on a finger, and a unit positioned on the hand having an electro-pneumatic control valve and some other components.

FIG. 2 shows a perspective view of an inflatable cuff 1 winded around a finger, in which cuff one of the light elements 3, 4 is schematically indicated. Also a unit 21 arranged on the hand is indicated, in which unit an electric circuit, the electric control valve 10 and a pressure transducer placed at the outlet of the control valve are arranged. The electric circuit in said unit is connected via the electric line 5b to the light elements 3, 4. The control valve 10 is connected via a PVC-line 5a to the pressure cuff 1. Said unit 21 is connected via an electric connection 22 and a PVC-line 23 respectively to a further electric circuit or processing unit and to the fluid container 12.

The principle of the measurement is based on identical pressure at all times in the cuff and in the arteries of the finger under the cuff. This requires the transmural pressure across the arterial wall to be zero and therefore the arterial diameter to be the unstretched diameter just before collapse. The so called lock-on procedure in this respect is of importance. In general, the servo loop will clamp the arterial diameter to a particular fixed value, thus making the pulsatile output signal of the photo-electric plethysmograph zero. Only when the artery is clamped at zero transmural pressure, is the arterial wall truly "unloaded" and the arterial pressure equals cuff pressure.

Furthermore, it is assumed during adjustment of the locking procedure that the effective predetermined cuff pressure is such that the venous and capillary system in the finger is sufficiently emptied by the pressure such that the photo-electric plethysmograph is only sensitive to the amount of blood in the artery. The locking subsequently proceeds in such a way that the cuff pressure is adjusted to a level below the systolic pressure level in the artery but above the diastolic pressure level of the artery. Next, the control loop is closed, the diameter of the artery being clamped to a value which is about equal to the unstretched diameter.

As illustrated in FIG. 3, a section is given of a single fluid flapper-nozzle system which is often used as material for pressure controlling purposes. The flow F of the fluid, such as liquid or gas, through such a system is equal to $F = \pi dhC\sqrt{2P/\rho}$ under certain limitations, in which P represents the pressure, d the diameter of the nozzle opening, and $\rho$ the density of the fluid flow.

The term $\pi dh$ is the so-called "curtain" surface of the nozzle member T, indicated separately in FIG. 3, in case a flapper V is at a distance h from the nozzle opening. The flow is turbulent, hence that is why the density $\pi$ of the fluid and not the viscosity appears in the formula. Hence that is why the term P is used. The constant C is about equal to 0.6. When the distance h is varied by moving the flapper, a flapper-nozzle system can be considered as a variable flow resistance equivalent to a transistor.

As illustrated in FIG. 4, a section is given of an arrangement in which often a flapper-nozzle system is taken up and which is equivalent to the resistance-transistor diagram indicated in the same figure. A restriction R in the flow F is applied as usual for obtaining a controlling pressure P which can be modulated by moving the flapper V. By means of this flapper V then the fluid flow F2 in the nozzle T is influenced such that the controlled flow F1 can be used for certain purposes, such as for example the displacement of a piston. In the case of the above mentioned device especially the pressure P, which is transferred to the pressure cuff, is of importance. This arrangement as stated is equivalent to the resistance-transistor diagram, indicated in FIG. 3, where the controlling signal S at the basis of the transistor influences the current F2 and thereby the current F1 and the pressure P.

This arrangement is disadvantageous herein that if in above device the pressure P has to be augmented in a fast manner, such as for example in case of hypertension patients more than 200 mm Hg in less than 50 ms, one eventually can do nothing more than closing the flapper-nozzle system. The flow for inflating the pressure cuff then is limited by the restriction R which really is not desired at all for a fast operation. In case one selects therefore a large fixed opening for the restriction this means a flapper-nozzle system of large dimensions and so a high use of air.

As illustrated in FIG. 5, the double flapper-nozzle system according to the invention is indicated by which the above mentioned problems are obviated. The balance connection is known from the electronic techniques, such as indicated in the same FIG. 5, in which a PNP and NPN transistor circuit is taken up between earth and power supply. The output signal U is influenced by the same controlling signal S by which the one transistor closes and the other just opens.

The double flapper-nozzle system in balance connection as indicated in FIG. 5 is controlled by the movement of the flapper V, while the nozzle member T1 serves as inlet and the nozzle member T2 serves as outlet of the liquid or gas. The pressure P at the outlet of the chamber K is transferred to the pressure cuff. Therefore, in this double flapper-nozzle system only one flapper-nozzle member is used in opposite sense for the liquid or gas flow, whereby it appeared that the constant C in the above mentioned formula for F has practically the same value.

The space around the nozzle opening of a single flapper-nozzle system, which otherwise is used as outlet, now is implemented as a chamber around the oppositely arranged nozzle openings and forms the inlet or supply to the fluid line of the pressure cuff.

An important advantage in this double flapper-nozzle system in balance connection according to the invention is that the restriction R is not required and can be omitted.

When using the double flapper-nozzle system from FIG. 5, the adjustment of both flapper-nozzle members is such that there is a large leakage flow from the inlet T1 via both opened flapper-nozzle members to the outlet T2. This is known as class A bias of an amplifier in electronics. From the further known tube or transistor bias adjustments type A/B, B and D, the type A/B adjustment is one having less leakage current but in case a large current is required, the transistors for example can be fully "opened". This can be attained in the double flapper-nozzle system with the aid of spring-mounted nozzle members.

This arrangement is indicated in FIG. 6, in which the material of the walls of both nozzle members T1 and T2 is made resilient.

An extremely effective device for the control of fluid flows and pressures and for the measurement of blood pressure in the finger is realized by means of the above mentioned embodiment of the electro-pneumatic control valve. By this the arterial pressure is continuously measured with the aid of the external pressure in the line 5a, connected to the control valve, which external pressure at any moment equals the intra-arterial pressure.

The requirement for compensating the pressure in the artery as soon as possible by means of the pressure of the pressure cuff, such that the transmural pressure continuously equals zero, necessitates the complete control loop to operate extremely fast and the control valve to alter the pressure immediately in response to the signal of the electronic circuit. For this purpose, for example, a piezo-electric element can be used to advantage for controlling the flapper.

The length of the connection between control valve and pressure cuff is in this case of importance as the pressure change effected by the control valve does not propagate through the line 5a faster than the sound velocity in air of 340 m/sec. Owing to this, some delay in the control loop comes about which can lead to instability. By giving the control valve a small dimension and light weight among others by using the presently available small electro-magnetic coupling motors for the movement of the flapper, this valve can be positioned near the pressure cuff and the finger or hand in a light loading manner, such that this delay is minimized. For the sake of having a lighter embodiment a piezoelectric element can be used to advantage instead of a coupling motor.

We claim:

1. An apparatus for continuously measuring blood pressure in a non-invasive manner, comprising:
   a pressurizable cuff adapted to be wrapped about a human extremity such as a finger;
   a light source and light detector, both being provided at the inner side of said pressure cuff for developing an electrical signal indicative of an amount of blood in said extremity;
   a control valve for controlling the pressure of fluid within the cuff; and
   an electronic circuit for controlling the control valve in response to the electrical signal so as to control the fluid pressure in the cuff to substantially follow the blood pressure within the extremity so that the arterial volume is maintained to a predetermined value, the fluid pressure providing an indication of the blood pressure, the control valve comprising:
   a valve chamber;
   a fluid inlet nozzle for admitting fluid from a fluid source into the chamber;
   a fluid exhaust nozzle for exhausting fluid from the chamber;
   an output port for transmitting a pressure in the chamber to the pressure cuff; and
   a single flapper member alternatively movable between a first position wherein it closes the fluid inlet nozzle while allowing the fluid exhaust nozzle to be open and a second position wherein it closes the exhaust nozzle while allowing the inlet nozzle to be open, there being a flow of fluid into the chamber through the inlet nozzle and a flow of fluid out of the chamber through the exhaust nozzle when the flapper member is at any position other than the first or second position.

2. An apparatus according to claim 1, wherein the nozzle are fabricated from a resilient material for controlling the bias of current flow from said fluid inlet nozzle to said fluid exhaust nozzle.

3. An apparatus according to claim 1 or 2, further including a piezoelectric element for moving the flapper member in accordance with a signal from the electronic circuit.

4. An apparatus according to claim 1 or 2 wherein the control valve is coupled to the pressure cuff with a tube maintained sufficiently short such that there is no significant pressure drop or pressure propagation delay therein.

5. An apparatus according to claim 3, wherein the control valve is coupled to the pressure cuff with a tube maintained sufficiently short such that there is no significant pressure drop or pressure propagation delay therein.

6. In a photo-electric plethysmograph blood pressure measuring apparatus including a pressurizable cuff adapted to be wrapped about a human extremity, such as a finger, a light source and light detector both being provided at an inner side of said pressure cuff for developing an electrical signal indicative of an amount of blood in the arteries of said extremity, a control valve for controlling the pressure of fluid within the cuff. and an electronic circuit for controlling the control valve in response to the electrical signal so as to control the fluid pressure in the cuff to substantially follow the blood pressure within the extremity so that the arterial volume is maintained to a predetermined value, the fluid pressure providing an indication of the blood pressure, the improvement wherein the control valve comprises:
   a valve chamber;
   a fluid inlet nozzle for admitting fluid from a fluid source into the chamber;
   a fluid exhaust nozzle for exhausting fluid from the chamber;
   an output port for transmitting a pressure in the chamber to the pressure cuff; and
   a single flapper member alternately movable between a first position wherein it closes the fluid inlet nozzle while allowing the fluid exhaust nozzle to be open and a second position wherein it closes the exhaust nozzle while allowing the inlet nozzle to be open, there being a flow of fluid into the chamber through the inlet nozzle and a flow of fluid out of the chamber through the exhaust nozzle when the flapper member is at any position other than the first or second position.

7. An improvement according to claim 6, wherein the nozzles are fabricated from a resilient material for controlling the bias of current flow from said fluid inlet nozzle to said fluid exhaust nozzle.

8. An improvement according to claim 6 or 7, further including a piezoelectric element for moving the flapper member in accordance with a signal from the electronic circuit.

9. An improvement according to claim 6 or 7 wherein the control valve is coupled to the pressure cuff with a tube maintained sufficiently short such that there is no significant pressure drop or pressure propagation delay therein.

10. An improvement according to claim 8, wherein the control valve is coupled to the pressure cuff with a tube maintained sufficiently short such that there is no significant pressure drop or pressure propagation delay therein.

* * * * *

UNITED STATES PATENT AND TRADEMARK OFFICE
CERTIFICATE OF CORRECTION

PATENT NO. : 4,406,289
DATED : September 27, 1983
INVENTOR(S) : Karel H. Wesseling and Wilhelmus H. Klawer It is certified that error appears in the above-identified patent and that said Letters Patent is hereby corrected as shown below:

On the title page the assignee should read as follows:

-- Nederlandse Centrale Organisatie Voor Toegepast-Natuurwetenschappelijk Onderzoek --.

Signed and Sealed this

Eighth Day of January 1985

[SEAL]

Attest:

*Attesting Officer*

GERALD J. MOSSINGHOFF

*Commissioner of Patents and Trademarks*